United States Patent [19]

Knapp et al.

[11] Patent Number: 5,159,062
[45] Date of Patent: Oct. 27, 1992

[54] SIGNAL PEPTIDE FOR THE SECRETION OF PEPTIDES IN *ESCHERICHIA COLI*

[75] Inventors: Stefan Knapp; Egon Amann; Karl-Josef Abel, all of Marburg, Fed. Rep. of Germany

[73] Assignee: Behringwerde Altiengesellschaft, Marburg, Fed. Rep. of Germany

[21] Appl. No.: 467,551

[22] Filed: Jan. 19, 1990

[30] Foreign Application Priority Data

Jan. 21, 1989 [DE] Fed. Rep. of Germany ....... 3901681

[51] Int. Cl.$^5$ ............................................. C07K 9/00
[52] U.S. Cl. ................................ 530/350; 530/825; 435/69.7; 435/69.8; 935/48
[58] Field of Search ...................... 530/825, 300, 350; 435/69.1, 69.8; 935/48

[56] References Cited

FOREIGN PATENT DOCUMENTS 0288451 10/1988 European Pat. Off. .

OTHER PUBLICATIONS

Amann et al., Gene, 69, 301–315 (1988).
Beattie et al., Journal of Bacteriology, 172, 6997–7004 (1990).
C. Hoffman et al., Proc. Natl. Acad. Sci. USA., vol. 82, pp. 5107–5111 (1985).
C. Manoil et al., Proc. Natl. Acad. Sci. USA, vol. 82, pp. 8129–8133 (1985).
S. Knapp et al., J. Bacteriol. Vol. 170, No. 11, pp. 5059–5066 (1988).
A. Friedman et al., Gene, vol. 18, pp. 289–296 (1982).
S. Henikoff et al., Gene, vol. 28, pp. 351–359 (1984).
W. Kramer et al., Nucl. Acids. Res., vol. 12, No. 24, pp. 9441–9456 (1984).
E. Amann et al. Gene, vol. 40, pp. 183–190 (1985).
Y. Kikuchi et al., Nucl. Acids Res., vol. 9, No. 21, pp. 5671–5679 (1981).
N. Movva et al., J. Biol. Chem., vol. 255, No. 1, pp. 27–29 (1980).
M. So et al., Proc. Natl. Sci. USA, vol. 77, No. 7, pp. 4011–4015 (1980).
C. Lee et al., Infection and Immunity, vol. 42, No. 1, pp. 264–268 (1983).
M. Yang et al., Nucl. Acids Res., vol. 11, No. 2, 237–249 (1983).
N. Sinha et al., Nucl. Acids Res., vol. 12, No. 11, pp. 4539–4557 (1984).

*Primary Examiner*—Richard A. Schwartz
*Assistant Examiner*—John L. LeGuyader
*Attorney, Agent, or Firm*—Finnegan, Henderson, Farabow, Garrett and Dunner

[57] ABSTRACT

The invention relates to a new signal peptide from *Bordetella pertussis* with the amino acid sequence M K K W F V A A G I G A G L L M L S S A A and to particularly suitable expression vectors with whose aid such signal sequences can be found and/or evaluated.

1 Claim, 4 Drawing Sheets

SIGNAL PEPTIDE FOR THE SECRETION OF PEPTIDES IN ESCHERICHIA COLI

The invention relates to the signal peptide of a protein from *Bordetella pertussis* which is able to direct heterologous proteins into the periplasmic space between the inner and outer membranes of Gram-negative species of bacteria. The invention additionally relates to DNA sequences which code for this signal peptide, to plasmids which contain a gene structure of this type, and to host organisms with plasmids of this type. The invention furthermore relates to plasmid vectors with whose aid it is possible to determine and compare the efficiency of known and new signal sequences. It is possible as a consequence of such comparative study for particularly efficient signal sequences to be identified, cloned and used in all three possible translation reading frames for the expression of heterologous proteins.

It is possible in principle to distinguish between two different types of signal sequences: a "hydrophobic" type and a "hydrophilic" type. The "hydrophobic" group of signal sequences usually comprises about 13-30 amino acids, whereas the "hydrophilic" group comprises about 12-70 amino acids. The signal sequence of the "hydrophobic" type can be divided into three structural elements. It is composed of a relatively hydrophilic $NH_2$ terminus with one or two basic amino acids, of an apolar, mostly hydrophobic block of seven or eight amino acids, and of a relatively hydrophilic COOH terminus which is terminated by an amino acid with a small side-chain. Such "hydrophobic" signal sequences guide proteins through the membrane of the endoplasmic reticulum (ER) and through bacterial membranes. Although bacterial and ER signal sequences differ slightly from one another, they are functionally interchangeable. The structure of the "hydrophilic" type differs greatly from that of the abovementioned "hydrophobic" type: there are no lengthy uninterrupted sections of hydrophobic amino acids in the "hydrophilic" type, but there are usually many basic and hydroxylated amino acids and few or no acidic amino acids. The "hydrophilic" type of signal sequences guides proteins into mitochondria, chloroplasts and, possibly, into peroxisomes too. It has no significance for the present invention.

Although, as shown above, the "hydrophobic" type of signal sequences of prokaryotic and eukaryotic origin have common characteristics and may be functionally interchangeable, there are also observable differences: thus, most of the prokaryotic signal sequences hitherto known have, by comparison with the "hydrophobic" type (=ER type) of eukaryotic signal sequences, a lower hydrophobicity in the apolar section plus, usually, an additional basic amino acid in the $NH_2$ region. This is possibly the reason why the natural signal sequence of a heterologous protein is usually less efficiently recognized and processed in microorganisms than is a bacterial signal sequence preceding this protein.

The secretion of a heterologous protein in *E. coli* usually takes place as transport through the inner membrane into the periplasmic space; only a few exceptions in which heterologous proteins are secreted into the surrounding medium are known. The transport of a heterologous protein into the periplasmic space in *E. coli* substantially corresponds functionally to the transport of a protein into the lumen of the endoplasmic reticulum of eukaryotic cells. It is possible as a consequence of this process for proteins to be correctly folded and for intramolecular disulfide bridges to be correctly produced in *E. coli* too. The signal sequence is eliminated by proteolysis by specific signal peptidases, and thus the mature, "processed" heterologous protein is synthesized in *E. coli*.

Some proteins are unstable after cytoplasmic expression in bacteria, for example *Escherichia coli*, and are very rapidly broken down again by proteases. This breakdown can be prevented by, inter alia, these proteins being, owing to a preceding, very efficient signal sequence, rapidly secreted into the periplasmic space. Hence the object was to isolate particularly efficient signal sequences and to design processes suitable for this.

Hoffman and Wright (Proc. Acad. Natl. Sci. USA; (1985) 82, 5107-5111) describe plasmids which code for the periplasmic alkaline phosphatase from *E. coli* (PhoA, EC 3.1.3.1) without the signal sequence belonging thereto. In in vitro fusions with fusion partners with their own signal sequence there is now secretion of active alkaline phosphatase in the form of a fusion protein, whereas when there is no fused-on signal sequence there is no detectable activity for the alkaline phosphatase released into the cytoplasm. Manoil and Beckwith (Proc. Natl. Acad. Sci. USA (1985) 82, 8129-8133) continued this work by placing the cDNA coding for PhoA without a signal sequence and 5 subsequent amino acids on the 3' side in front of the transposon Tn5 (loc. cit.) and were thus able to show that fusions not only with secreted proteins but also with membrane proteins result in active PhoA. The said construct "TnPhoA" is consequently suitable for identifying signal sequences or structures resembling signal sequences.

S. Knapp and J. Mekalanos (J. Bacteriology (1988) 170, 5059-5066) have now generated, by means of TnPhoA mutagenesis, mutants in *Bordetella pertussis* which are influenced by modulation signals (in this case nicotinic acid and $MgSO_4$), with the majority of these mutants being repressed and some being activated, which suggests that there are at least two trans-acting regulatory genes. We have found that the mutant SK6 mentioned therein contains a new and very efficient signal sequence.

This new signal sequence belongs to a secretory protein from *Bordetella pertussis* and has the following sequence (cf. Tab. 2 and 3)

M K K W F V A A G I G A G L L M L S S A A.

Figure 1A:
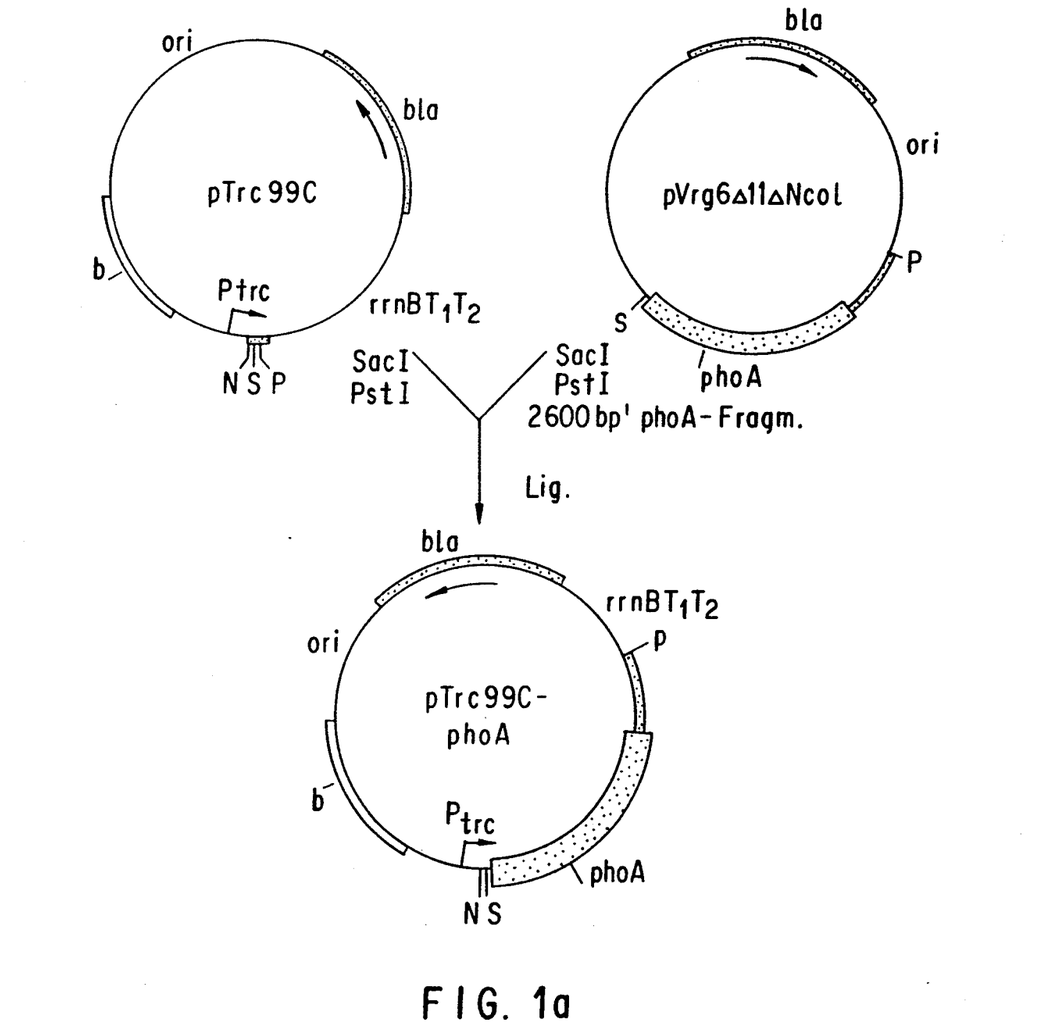
Figure 1B:
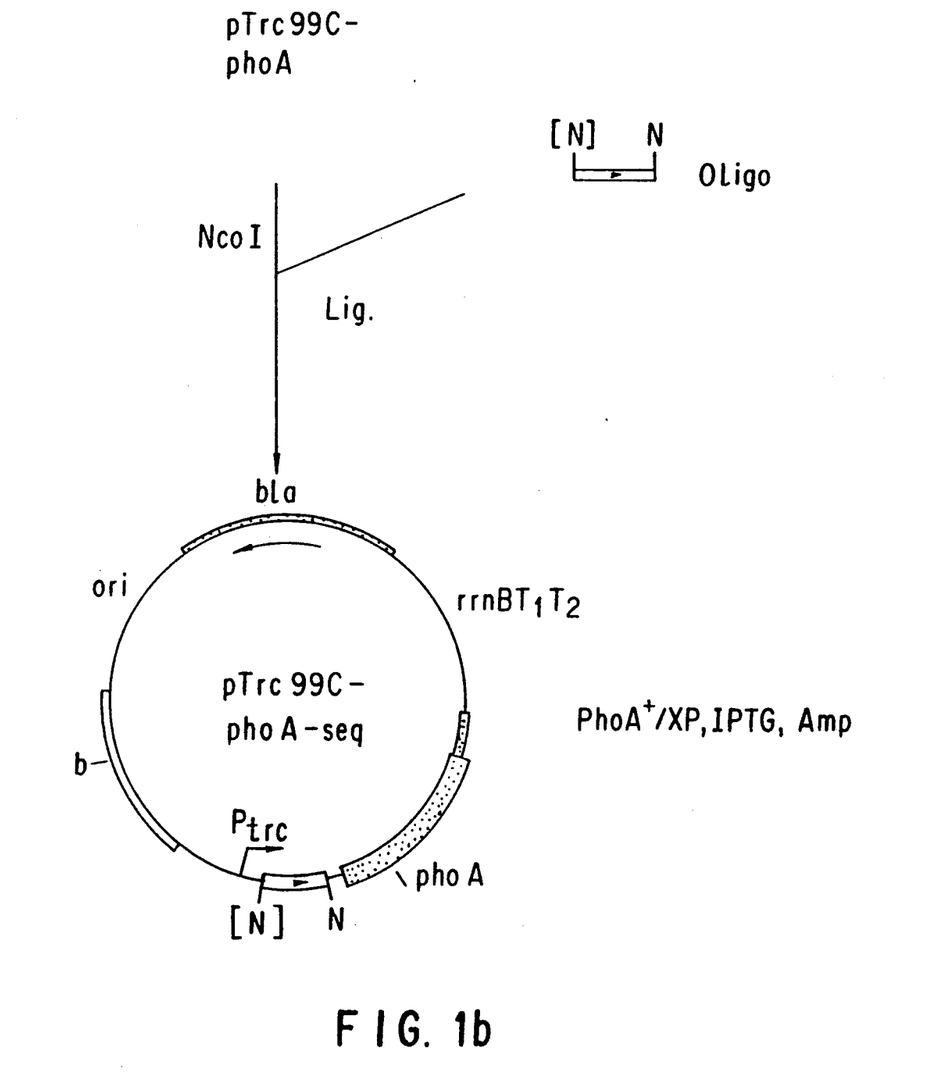

Also described are PhoA-containing plasmids which, on the one hand, are very well suited as "signal-sequence cloning vectors" and, on the other hand, make it possible to compare quantitatively various signal sequences in terms of their "secretion efficiency". Particularly useful for both purposes is the vector pTrc99C-PhoA (FIG. 1, Tab. 1 and Example 2). This vector has been constructed from pTrc99C (Amann et al. Gene 69 (1988) 301-315) and from a PhoA DNA which has been modified to that effect and has no signal peptide sequence, in such a way that the structural gene for PhoA is located in the correct reading frame with respect to the translation initiation codon of pTrc99C, and an NcoI cleavage site has been generated directly at the 5' end of the PhoA structural gene (without signal sequence).

Accordingly, the invention relates to:
a) the signal sequence

M K K W F V A A G I G A G L L M L S S A A b) plasmids which carry a sequence of this type,
c) the use thereof for the secretion of proteins, and
d) plasmids which are particularly suitable for the cloning and quantitative evaluation of signal sequences, due to the fact that a strong promoter which can be regulated, such as trc, is followed by the lacZ ribosome-binding site (RBS) and by a vector-encoded translation initiation codon at a distance from the lacZ RBS which is optimized for high expression, with an NcoI cleavage site being present directly at the 5' end of the PhoA structural gene which has no signal sequence, but having been deleted from within the PhoA sequence by mutation, and with pTrc99C-PhoA being preferred.

BRIEF DESCRIPTION OF THE DRAWINGS

FIG. 1 (Parts a and b): Construction of plasmid pTrc99C-phoA.

EXAMPLE 1

Identification and isolation of the *Bordetella pertussis* signal sequence

The transposon TnPhoA used hereinafter is a derivative of the transposon Tn5. TnPhoA. carries in the left IS50 insertion element an *E. coli* PhoA structural gene derivative which has no signal sequence. The latter was constructed by Manoil and Beckwith (loc. cit.) in such a manner that when TnPhoA has transposed into a chromosomal or plasmid-encoded gene the result is a PhoA-positive gene fusion only if the reading frames of the *E. coli* PhoA structural gene from TnPhoA and the signal sequence of the structural gene affected by the transposition coincide. It is easy to identify such PhoA positive colonies using the dyestuff indicator 5-bromo-4-chloro-indoxyl phosphate toluidine (XP). The described technique was used to carry out a TnPhoA mutagenesis in the *Bordetella pertussis* wild strain 18323 (Knapp and Mekalanos (1988) loc. cit.). This resulted, inter alia, in the generation of the PhoA-positive TnPhoA mutant SK6, whose TnPhoA gene fusion is called vrg6. The vrg6 gene fusion was cloned on a 20 kb BamHI fragment in the vector plasmid pBR322 as follows: genomic DNA of the mutant SK6 was cleaved with BamHI and ligated with pBR322 DNA cut with BamHI and was transformed into the *E. coli* strain CC118 (=PhoA negative). Clones which contain the genomic fragment with the TnphoA gene fusion were selected on kanamycin/ampicillin agar plates (TnphoA codes like Tn5 for a kanamycin-resistance gene which is located between the 5' phoA portion of TnphoA and the unique BamHI cleavage site within TnphoA).

A genomic BamHI fragment from a TnphoA. mutant which has kanamycin resistance must therefore also carry the PhoA structural gene and the genomic *B. pertussis* DNA, located upstream, as far as the next genomic BamHI cleavage site. In the case of the BamHI fragment which is 20 kb in size and carries the vrg6 gene fusion, about 14 kb correspond to genomic *B. pertussis* DNA and about 6 kb correspond to TnphoA-encoding DNA. Transcriptional and translational regulation sequences of the vrg6 gene fusion were further localized. For this purpose, the BamHI fragment which is 20 kb in size was subjected to restriction analysis, and subfragments which carry the entire PhoA sequence from TnphoA but, compared to the 20 kb fragment, truncated *B. pertussis* DNA regions were cloned into pBR322 and pUC18. The deletion derivatives obtained in this way were recloned into the plasmid pLAFR2 which is able to replicate in *B. pertussis* (Friedmann et al. (1982), Gene 18, 289-196) and, after conjugative transfer into *B. pertussis*, examined for PhoA activity susceptible to modulation. In this way a PstI fragment which is about 3.2 kb in size was identified and subcloned into pUC18 (called pUC-PI hereinafter) which now contains only about 500 base-pairs of *B. pertussis* DNA upstream of the TnphoA insertion site of the vrg6 gene fusion and is PhoA positive in *B. pertussis* after induction. Since the PhoA activity of *B. pertussis* derivatives which contain the cloned BamHI fragment which is 20 kb in size or the PstI fragment which is 3.2 kb in size do not differ essentially in their phosphatase activity, the transcriptional and translational regulation sequences of the vrg6 gene fusion on the latter fragment must still be completely present. Starting from pUC-PI, deletions were introduced into the DNA region located 500 base-pairs upstream from the TnphoA insertion site using the enzymes exonuclease III and S1 nuclease by the method of Henikoff ((1984) Gene 28, 351-359). This resulted, inter alia, in the two pUC-PI derivatives vrg6-delta12 and vrg6-delta11, vrg6-delta12 still contains about 200 base-pairs *B. pertussis*-specific DNA upstream from the TnphoA insertion site and is likewise PhoA positive. DNA sequencing was used to determine the *B. pertussis* signal sequence on this recombinant plasmid.

The signal sequence is as follows:

M K K W F V A A G I G A G L L M L S S A A (cf. also Tab. 2). The *B. pertussis* signal sequence characterized in this way comprises 21 amino acids and was subsequently prepared and cloned as described in Example 3 and is suitable for the secretion of heterologous proteins.

vrg6-delta11 contains only four *B. pertussis*-specific nucleotides upstream from the TnphoA insertion site, followed by a pUC18-specified SacI cleavage site (Tab. 1). PstI/SacI cleavage of the vrg6-delta11 DNA results in the complete PhoA structural gene from TnphoA, which has no signal sequence and is on a fragment which is about 2.6 kb in size and which serves as a source of the phoA structural gene which has no signal sequence in Example 2.

EXAMPLE 2

Construction of a vector plasmid (pTrc99C-phoA) for the cloning and comparative efficiency measurement of signal sequences.

The construction of the vector plasmid pTrc99C-phoA is described hereinafter. This vector plasmid carries as essential element the phoA structural gene which has already been described above, has no signal sequence and was isolated from TnphoA. The phoA structural gene carries an internal NcoI cleavage site. This cleavage site was eliminated by the method of site-directed mutagenesis while retaining the amino acid sequence.

Figure 3:
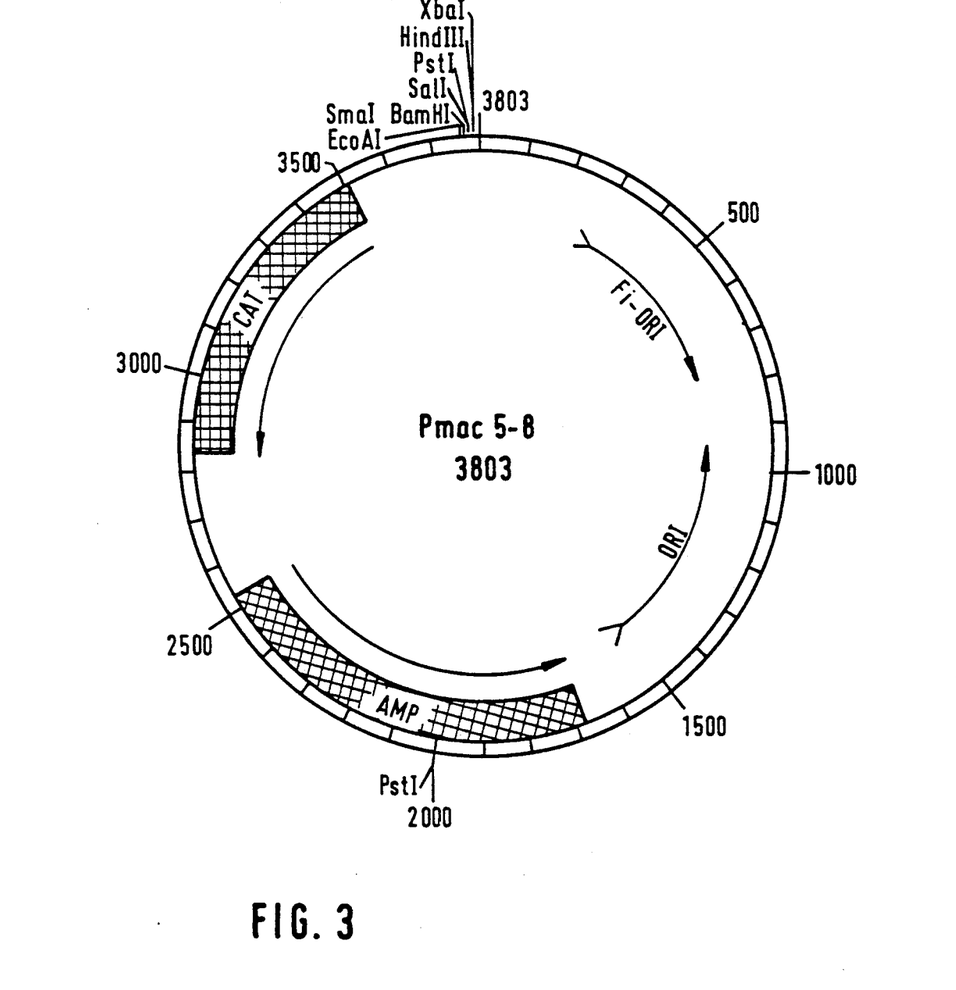
FIG. 3: Plasmid pmac 5-8 3803.
Furthermore, the invention is further detailed in the examples and the patent claims.

For this purpose, initially the recombinant PhoA-negative plasmid pvrg6-delta11 (see Example 1) was cleaved with EcoRI, and the fragment which is 330 base-pairs in size from the internal region of the phoA structural gene was isolated. This fragment, which contains the NcoI cleavage site which is to be mutated, was ligated into the EcoRI site of the mutagenesis vector pMa5-8 (FIG. 3). The resulting plasmid pMa5-8-EcoRI330 was isolated and used to prepare a single strand. The single strand with the cloned EcoRI fragment obtained in this way was then isolated by known methods and subjected to the published gapped-duplex mutagenesis protocol (Kramer et al. (1984) Nucl. Acids Res. 12, 9441-9456), using the following oligodeoxynucleotide:

5' ATCGATATTGCCGTGGTACGTTGCTTTC 3'

A plasmid which had the desired NcoI mutation was identified by appropriate restriction analysis, and the relevant region was sequenced and confirmed as correct. Subsequently the EcoRI fragment which is 330 base-pairs in size was reisolated from this plasmid and sited in place of the corresponding fragment of the plasmid pvrg-6-delta11. For this purpose, pvrg-6-delta11 was partially digested with EcoRI, and a fragment which was shorter by 330 base-pairs than the starting plasmid pvrg-delta11 (about 6700 bp), which had been linearized by partial EcoRI digestion, was isolated. The EcoRI fragment of this size (about 6400 bp) was treated with alkaline phosphatase and ligated to the mutated EcoRI fragment which was 330 base-pairs in size, and the ligation mixture was transformed into $E.\ coli$. Recombinant plasmids which contain a restored phoA. structural gene with the correctly inserted 330 base-pair EcoRI fragment were identified by restriction analysis and DNA sequencing. A recombinant plasmid of this type. pvrg6-delta11-deltaNcoI, was replicated and used to construct the hybrid plasmid pTrc99C-phoA. For this purpose, a SacI-ScaI fragment which was about 2600 base-pairs in size was isolated from pvrg6-delta11-deltaNcoI. In the next step the SacI-ScaI fragment which is about 900 base-pairs in size from pTrc99C (Amann et al. (1988) Gene 69, 301-315) was replaced by this SacI-ScaI fragment which is about 2600 base-pairs in size. The resulting recombinant plasmid pTrc99C-phoA now carries, as a result of the above manipulations, a unique NcoI cleavage site directly at the 5' end of the phoA structural gene which has no signal sequence, and it can used, as shown in the following example, for cloning any desired synthetic or natural signal sequences. pTrc99C-phoA carries the structural gene of phoA in the correct reading frame with respect to the translation initiation codon of the expression vector pTrc99C but is unable, because of the absence of the phoA. signal sequence, to bring about in transformed $Escherichia\ coli$ cells the synthesis of an enzymatically active alkaline phosphatase and is therefore suitable as a "signal-sequence cloning vector". In addition, pTrc99C-phoA carries, upstream from the hybrid trc promoter (Amann and Brosius (1985) Gene 40, 183-190), the lacZ ribosome-binding site (RBS) and a translation initiation codon at a distance from the lacZ RBS which is optimized for high expression. $E.\ coli$ cells which contain the recombinant plasmid pTrc99C-phoA do not produce any plasmid-encoded biologically active alkaline phosphatase activity because the phoA structural gene of this plasmid lacks the signal sequence. PhoA-positive colonies can now be generated by placing a DNA fragment coding for a signal sequence in front of the phoA structural gene in the correct reading frame. This can take place by cutting pTrc99C-phoA with NcoI and inserting synthetic DNA fragments which code for signal sequences into this vector DNA. Bacterial colonies which carry hybrid plasmids of this manipulation can now easily be identified by means of their new PhoA-positive phenotype using the dyestuff indicator XP which has already been described above. The principle which has been presented is explained hereinafter in the form of exemplary embodiments. Cloning of signal sequences of various secretory proteins into the pTrc99C-phoA vector results in isogenic recombinant plasmids which differ only in the signal sequence. For this reason, the phoA activity of the $E.\ coli$ cells which contain such constructs provides a measure of the efficiency of the relevant cloned signal sequences.

Another possible use of the vector pTrc99C-phoA comprises the cloning of the synthetic DNA fragments which do not code for an unambiguously defined signal sequence but are degenerate in such a way that a plurality of amino acids is possible for each position of the signal sequence. This is to a certain extent a shotgun cloning, and the phoA activity measurement which is now possible due to the vector represents a measure of the efficiency of the artificial signal sequence. It is possible to use this method to prepare and evaluate new signal sequences which can be used for the heterologous expression of cloned genes.

The principle of the construction of pTrc99C-phoA is illustrated in FIG. 1. The abbreviations mean: N=NcoI, S=SacI, P=PstI, [N]=NcoI site is not regenerated after ligation, 'phoA=phoA. structural gene which has no signal sequence, arrows indicate the direction of transcription or the $NH_2 \rightarrow COOH$ orientation of translated regions. Oligo means=synthetic oligonucleotide sequence. Tab. 1 shows the relevant cloning and translation initiation region of pTrc99C-phoA.

EXAMPLE 3

DNA synthesis and cloning of the $Bordetella\ pertussis$ signal sequence and of five other naturally occurring microbial signal sequences of secretory proteins.

The vector pTrc99C-phoA was used to clone six different signal sequences whose amino acid sequences are depicted in Tab. 2. Five other signal sequences, besides the new $Bordetella\ pertussis$ signal sequence, were selected on the basis of the following criteria:
a) Signal sequence of a periplasmic protein
   Alkaline phosphatase (phoA) from $E.\ coli$ (Kikuchi et al. (1981) Nucleic Acid Res. 9, 5671-5678)
b) Signal sequence of an outer membrane protein
   Outer membrane protein (ompA) from $E.\ coli$ (Movva et al. (1980) J. Biol. Chem. 255, 27-29)
c) Signal sequences of three proteins secreted into the medium
   Heat stable toxin I (STI) from $E.\ coli$ (So and McCarthy (1980) Proc. Natl. Acad. Sci. USA 77, 4011-4015)
   Heat stable toxin II (STII) from $E.\ coli$ (Lee et al. (1983) Infect. Immun. 42, 264-268)
   Amylase from $Bacillus\ subtilis$ (Yang et al (1983) Nucleic Acids Res. 11, 237-249)

The following simplified nomenclature has been used for the synthesis and cloning of these signal sequences:

| |
|---|
| *Bordetella pertussis* vrg-6 signal sequence = Seq 1 |
| PhoA signal sequence = Seq 2 |
| OmpA signal sequence = Seq 3 |
| STI signal sequence = Seq 4 |
| STII signal sequence = Seq 5 |
| *Bacillus subtilis* amylase signal sequence = Seq 6 |

All six signal sequences mentioned were prepared by DNA synthesis. The DNA fragments synthesized for this purpose (depicted in Tab. 3) were cloned and identified in the test vector pTrc99C-phoA using the selection for alkaline phosphatase described in Example 2. The synthetic DNA fragments encoding the signal sequence were designed in such a way that, after insertion in the correct orientation in the vector pTrc99C-phoA, only one NcoI site is regenerated, specifically downstream from the region encoding the signal sequence (cf. also FIG. 1, Tab. 3 and Tab. 4). It is thus possible for this NcoI site to be used further, as further detailed in Example 4, as cloning site for the insertion of heterologous genes into the pSEC vectors (pSEC=secretion).

The twelve DNA fragments shown in Tab. 3 were synthesized by known methods (Sinha et al. (1984) Nucl. Acids Res. 12, 4539-4557) using β-cyanoethylamidites. The syntheses were carried out by the phosphite triester method (Letsinger (1975) J. Amer. Chem. Soc. 97, 3278; Letsinger (1976) J. Amer. Chem. Soc. 98, 3655) using a Biosearch synthesizer. After cleavage off the carrier (CPG) with concentrated ammonia at room temperature for 5-8 h, and after the protective groups on the bases had been cleaved off in the same solution at 55° C. for about 12 h, the oligodeoxynucleotides were purified by gel electrophoresis or reverse-phase HPLC. The oligodeoxynucleotides were taken up in annealing buffer (100 mM NaCl, 10 mM TRIS-Cl (pH 7.8), 0.1 mM EDTA), molar amounts of each strand mixed, incubated at 95° C. for 5 min and slowly cooled to room temperature. The double-stranded DNA fragments have at the 5' ends single-stranded regions which are four bases long and are complementary to an NcoI recognition site. The test vector pTrc99C-phoA was linearized with NcoI and ligated in various mixtures together with hybridized DNA fragments. Competent *E. coli* cells were transformed with the ligation mixtures by known methods, plated out on LB/amp agar plates and incubated at 37° C. overnight. The colonies were transferred by the replica-plating method to LB/Amp/XP/IPTG indicator plates and again incubated at 37° C. PhoA-positive colonies have a blue color on this indicator plate. Plasmid DNA of these colonies was isolated and sequenced, and it was possible to confirm the correct orientation of the synthetic DNA fragments as well as the expected correct signal sequence for the six abovementioned examples. The plasmids which were obtained in this way and had the particular signal sequence confirmed as correct by sequencing were called, in accordance with the above table, pTrc99C-phoA-Seq-1, -2, -3, -4, -5 and -6. It is now possible under standardized conditions to compare and evaluate, on the basis of the extinction (measurement of the liberated dyestuff), these signal sequences, those found from *B. pertussis* being among the relatively strongest.

EXAMPLE 4

Construction of the secretion vectors pSEC-Bp-1, pSEC-Bp-2 and pSEC-Bp-3

Figure 2:
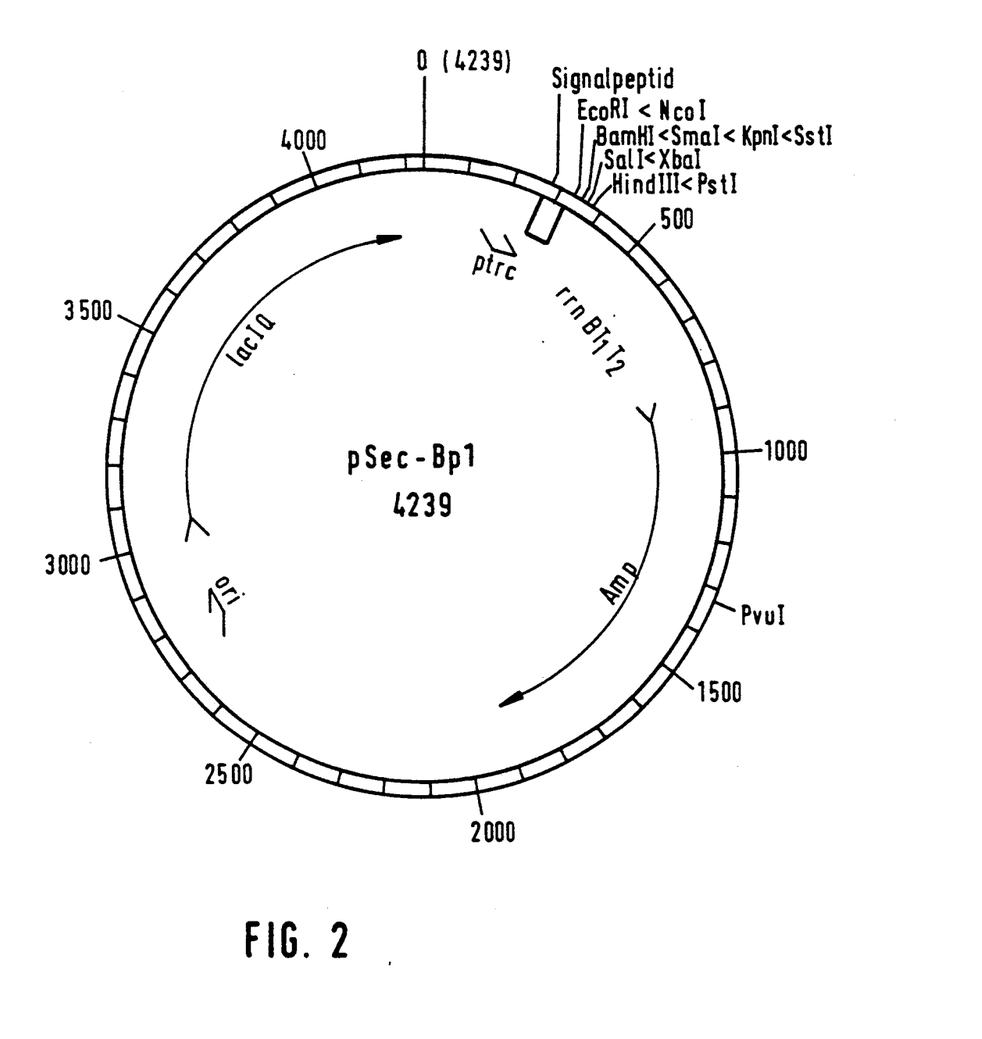
FIG. 2: Plasmid pSec-Bp1 4239.

Plasmid DNA of the clone pTrc99C-phoA-Seq-1 was digested with SacI and ScaI, and the fragment which is about 3.1 kb in size was isolated. This fragment carries only pTrc99C-specific sequences in addition to the *B. pertussis* signal sequence (see also FIG. 1). This fragment was ligated, in each of three separate mixtures, with one of the approximately 0.9 kb SacI/ScaI fragments of the plasmids pTrc97A, pTrc97B and pTrc97C (Amann et al. loc. cit.), and the resulting plasmids were called pSEC-Bp-1, pSEC-Bp-2 and pSEC-Bp-3. This manipulation made use of the long polylinker region of the plasmids pTrc97A, pTRC97B and pTrc97C in order to make available in all three reading frames a plurality of restriction sites downstream from the region encoding the *Bordetella pertussis* signal sequence (Tab. 4). It is possible in analogy to these constructions to prepare similar secretion vectors for the expression and secretion of heterologous proteins by use of the plasmids pTrc99C-phoA-Seq-2, -3, -4, -5 and -6. The secretion vectors prepared in this way differ in their relative efficiency and in the cellular location of the expressed products in accordance with the origin of the signal sequence used in each case. As an example, FIG. 2 shows the plasmid structure of pSEC-BP1, and Tab. 5 shows the complete DNA sequence of pSEC-BP1, where xxx stands for a start or stop codon.

Legend to FIG. 1:
Map of the plasmids pMAC5-8 (=pMA5-8 and pMC5-8).
F1-ORI: Origin of replication of the phage f1;
ORI: Origin of replication of the ColE1 type;
CAT: Coding region for chloramphenicol acetyltransferase;
AMP: Coding region for β-lactamase.
pMA5-8 carries an amber mutation in CAT (A at position 3409) and pMC5-8 carries an amber mutation in AMP (C at position 2238).

TAB. 1

TAB. 2

| -30 | -20 | -10 | -1 | | Amino-säuren |
|---|---|---|---|---|---|
| | M K | W F V A A G I G A | G L L M L S S A | A | B.p. | 21 |
| | M K | Q S T I A L A L L P | L L F T P V T K | A | E.c. phoA | 21 |
| | M K | K T A I A I A V A L | A G F A T V A Q | A | E.c. ompA | 21 |
| | M K | K L M L A I F F S V | L S F P S F S Q | S | E.c. ST I | 21 |
| | M K K | N I A F L L A S M F V | F S I A T N A Y | A | E.c. ST II | 23 |
| M F A K R F K T S L L P | L F A G F L L L F H L | V L A G P A A | S | B.s. Amylase | 32 |

TAB. 3

*Bordetella pertussis* signal sequence

5' C ATG AAA AAG TGG TTC GTT GCT GCC GGC ATC GGC GCT GCC GGA CTC ATG CTC TCC AGC GCC GC
   TTT TTC ACC AAG CAA CGA CGG CCG CGA CGG CCT GAG TAC GAG AGG TCG CGG CGG TAC 5'

*E. coli* phoA signal sequence

5' C ATG AAA CAA AGC ACT ATT GCA CTC TTA CCG TTA CTG TTT ACC CCT GTG ACA AAA GC
   TTT GTT TCG TGA TAA CGT GAG AAT GGC AAT GAC AAA TGG GGA CAC TGT TTT CGG TAC 5'

*E. coli* ompA signal sequence

5' C ATG AAA AAG ACA GCT ATC GCG ATT GCA GTG GCA CTG GCT GGT TTC GCT ACC GTA GCG CAG GC
   TTT TTC TGT CGA TAG CGC TAA CGT CAC CGT GAC CGA CCA AAG CGA TGG CAT CGC GTC CGG TAC 5'

*E. coli* heat-stable toxin I signal sequence

5' C ATG AAA AAG CTA ATG GCA ATT TTT ATT TCT GTA TTA TCT TTC CCC TCT TTT AGT CAG TCA CC
   TTT TTC GAT TAC AAC CGT TAA AAA TAA AGA CAT AAT AGA AAG GGG AGA AAA TCA GTC AGT GGG TAC 5'

*E. coli* heat-stable toxin II signal sequence

5' C ATG AAA AAG AAT ATC GCA TTT CTT CTT GCA TCT ATG TTC GTT TTT TCT ATT GCT ACA AAT GCC TAT GC
   TTT TTC TTA TAG CGT AAA GAA GAA CGT AGA TAC AAG CAA AAA AGA TAA CGA TGT TTA CGG ATA CGG TAC 5'

*Bacillus subtilis* Amylase signal sequence

5' C ATG TTT GCA AAA CGA TTC AAA ACC TCT TTA CTG CCG TTA TTC GCT GGA TTT TTA TTG CTG TTT CAT TTG GTT
   AAA CGT TTT GCT AAG TTT TGG AGA AAT GAC GGC AAT AAG CGA CCT AAA AAT AAC GAC AAA GTA AAC CAA

CTG GCA GGA CCG GCG GCT GCG AGT CC
GAC CGT CCT GGC CGC CGA CGC TCA GGG TAC 5'

TAB. 5

Sequence 7/1

```
   1  GTTTGACAGC TTATCATCGA CTGCACGGTG CACCAATGCT TCTGGCGTCA
  51  GGCAGCCATC GGAAGCTGTG GTATGGCTGT GCAGGTCGTA AATCACTGCA
 101  TAATTCGTGT CGCTCAAGGC GCACTCCCGT TCTGGATAAT GTTTTTTGCG
                                                    -35
 151  CCGACATCAT AACGGTTCTG GCAAATATTC TGAAATGAGC TGTTGACAAT
         trcP        -10
 201  TAATCATCCG GCTCGTATAA TGTGTGGAAT TGTGAGCGGA TAACAATTTC
                        M  K  K  W  F  V  A  A  G  I  G
 251  ACACAGGAAA CAGACCATGA AAAAGTGGTT CGTTGCTGCC GGCATCGGCG
                           ***
       A  G  L  L  M  L  S  S  A  A
 301  CTGCCGGACT CATGCTCTCC AGCGCCGCCA TGGAATTCGA GCTCGGTACC
                                 NcoI     EcoRI    SstI     KpnI
 351  CGGGGATCCT CTAGAGTCGA CCTGCAGGCA TGCAAGCTTG GCTGTTTTGG
       SmaI   BamHI   XbaI    SalI   PastI  SphI   HindIII
 401  CGGATGAGAG AAGATTTTCA GCCTGATACA GATTAAATCA GAACGCAGAA
           ***                  ***        ***
 451  GCGGTCTGAT AAAACAGAAT TTGCCTGGCG GCAGTAGCGC GGTGGTCCCA
 501  CCTGACCCCA TGCCGAACTC AGAAGTGAAA CGCCGTAGCG CCGATGGTAG
 551  TGTGGGGTCT CCCCATGCGA GAGTAGGGAA CTGCCAGGCA TCAAATAAAA
 601  CGAAAGGCTC AGTCGAAAGA CTGGGCCTTT CGTTTTATCT GTTGTTTGTC
 651  GGTGAACGCT CTCCTGAGTA GGACAAATCC GCCGGGAGCG GATTTGAACG
 701  TTGCGAAGCA ACGGCCCGGA GGGTGGCGGG CAGGACGCCC GCCATAAACT
 751  GCCAGGCATC AAATTAAGCA GAAGGCCATC CTGACGGATG GCCTTTTTGC
 801  GTTTCTACAA ACTCTTTTTG TTTATTTTTC TAAATACATT CAAATATGTA
 851  TCCGCTCATG AGACAATAAC CCTGATAAAT GCTTCAATAA TATTGAAAAA
 901  GGAAGAGTAT GAGTATTCAA CATTTCCGTG TCGCCCTTAT TCCCTTTTTT
 951  GCGGCATTTT GCCTTCCTGT TTTTGCTCAC CCAGAAACGC TGGTGAAAGT
1001  AAAAGATGCT GAAGATCAGT TGGGTGCACG AGTGGGTTAC ATCGAACTGG
1051  ATCTCAACAG CGGTAAGATC CTTGAGAGTT TTCGCCCCGA AGAACGTTTT
1101  CCAATGATGA GCACTTTTAA AGTTCTGCTA TGTGGCGCGG TATTATCCCG
1151  TGTTGACGCC GGGCAAGAGC AACTCGGTCG CCGCATACAC TATTCTCAGA
1201  ATGACTTGGT TGAGTACTCA CCAGTCACAG AAAAGCATCT TACGGATGGC
1251  ATGACAGTAA GAGAATTATG CAGTGCTGCC ATAACCATGA GTGATAACAC
1301  TGCGGCCAAC TTACTTCTGA CAACGATCGG AGGACCGAAG GAGCTAACCG
1351  CTTTTTTGCA CAACATGGGG GATCATGTAA CTCGCCTTGA TCGTTGGGAA
1401  CCGGAGCTGA ATGAAGCCAT ACCAAACGAC GAGCGTGACA CCACGATGCC
1451  TACAGCAATG GCAACAACGT TGCGCAAACT ATTAACTGGC GAACTACTTA
1501  CTCTAGCTTC CCGGCAACAA TTAATAGACT GGATGGAGGC GGATAAAGTT
1551  GCAGGACCAC TTCTGCGCTC GGCCCTTCCG GCTGGCTGGT TTATTGCTGA
1601  TAAATCTGGA GCCGGTGAGC GTGGGTCTCG CGGTATCATT GCAGCACTGG
1651  GGCCAGATGG TAAGCCCTCC CGTATCGTAG TTATCTACAC GACGGGGAGT
1701  CAGGCAACTA TGGATGAACG AAATAGACAG ATCGCTGAGA TAGGTGCCTC
1751  ACTGATTAAG CATTGGTAAC TGTCAGACCA AGTTTACTCA TATATACTTT
1801  AGATTGATTT AAAACTTCAT TTTTAATTTA AAAGGATCTA GGTGAAGATC
```

TAB. 5-continued

Sequence 7/1

| | | | | | |
|---|---|---|---|---|---|
| 1851 | CTTTTTGATA | ATCTCATGAC | CAAAATCCCT | TAACGTGAGT | TTTCGTTCCA |
| 1901 | CTGAGCGTCA | GACCCCGTAG | AAAAGATCAA | AGGATCTTCT | TGAGATCCTT |
| 1951 | TTTTTCTGCG | CGTAATCTGC | TGCTTGCAAA | CAAAAAAACC | ACCGCTACCA |
| 2001 | GCGGTGGTTT | GTTTGCCGGA | TCAAGAGCTA | CCAACTCTTT | TTCCGAAGGT |
| 2051 | AACTGGCTTC | AGCAGAGCGC | AGATACCAAA | TACTGTCCTT | CTAGTGTAGC |
| 2101 | CGTAGTTAGG | CCACCACTTC | AAGAACTCTG | TAGCACCGCC | TACATACCTC |
| 2151 | GCTCTGCTAA | TCCTGTTACC | AGTGGCTGCT | GCCAGTGGCG | ATAAGTCGTG |
| 2201 | TCTTACCGGG | TTGGACTCAA | GACGATAGTT | ACCGGATAAG | GCGCAGCGGT |
| 2251 | CGGGCTGAAC | GGGGGGTTCG | TGCACACAGC | CCAGCTTGGA | GCGAACGACC |
| 2301 | TACACCGAAC | TGAGATACCT | ACAGCGTGAG | CTATGAGAAA | GCGCCACGCT |
| 2351 | TCCCGAAGGG | AGAAAGGCGG | ACAGGTATCC | GGTAAGCGGC | AGGGTCGGAA |
| 2401 | CAGGAGAGCG | CACGAGGGAG | CTTCCAGGGG | GAAACGCCTG | GTATCTTTAT |
| 2451 | AGTCCTGTCG | GGTTTCGCCA | CCTCTGACTT | GAGCGTCGAT | TTTTGTGATG |
| 2501 | CTCGTCAGGG | GGGCGGAGCC | TATGGAAAAA | CGCCAGCAAC | GCGGCCTTTT |
| 2551 | TACGGTTCCT | GGCCTTTTGC | TGGCCTTTTG | CTCACATGTT | CTTTCCTGCG |
| 2601 | TTATCCCCTG | ATTCTGTGGA | TAACCGTATT | ACCGCCTTTG | AGTGAGCTGA |
| 2651 | TACCGCTCGC | CGCAGCCGAA | CGACCGAGCG | CAGCGAGTCA | GTGAGCGAGG |
| 2701 | AAGCGGAAGA | GCGCCTGATG | CGGTATTTTC | TCCTTACGCA | TCTGTGCGGT |
| 2751 | ATTTCACACC | GCATATGGTG | CACTCTCAGT | ACAATCTGCT | CTGATGCCGC |
| 2801 | ATAGTTAAGC | CAGTATACAC | TCCGCTATCG | CTACGTGACT | GGGTCATGGC |
| 2851 | TGCGCCCCGA | CACCCGCCAA | CACCCGCTGA | CGCGCCCTGA | CGGGCTTGTC |
| 2901 | TGCTCCCGGC | ATCCGCTTAC | AGACAAGCTG | TGACCGTCTC | CGGGAGCTGC |
| 2951 | ATGTGTCAGA | GGTTTTCACC | GTCATCACCG | AAACGCGCGA | GGCAGCAGAT |
| 3001 | CAATTCGCGC | GCGAAGGCGA | AGCGGCATGC | ATTTACGTTG | ACACCATCGA |
| 3051 | ATGGTGCAAA | ACCTTTCGCG | GTATGGCATG | ATAGCGCCCG | GAAGAGAGTC |
| 3101 | AATTCAGGGT | GGTGAATGTG | AAACCAGTAA | CGTTATACGA | TGTCGCAGAG |
| 3151 | TATGCCGGTG | TCTCTTATCA | GACCGTTTCC | CGCGTGGTGA | ACCAGGCCAG |
| 3201 | CCACGTTTCT | GCGAAAACGC | GGGAAAAAGT | GGAAGCGGCG | ATGGCGGAGC |
| 3251 | TGAATTACAT | TCCCAACCGC | GTGGCACAAC | AACTGGCGGG | CAAACAGTCG |
| 3301 | TTGCTGATTG | GCGTTGCCAC | CTCCAGTCTG | GCCCTGCACG | CGCCGTCGCA |
| 3351 | AATTGTCGCG | GCGATTAAAT | CTCGCGCCGA | TCAACTGGGT | GCCAGCGTGG |
| 3401 | TGGTGTCGAT | GGTAGAACGA | AGCGGCGTCG | AAGCCTGTAA | AGCGGCGGTG |
| 3451 | CACAATCTTC | TCGCGCAACG | CGTCAGTGGG | CTGATCATTA | ACTATCCGCT |
| 3501 | GGATGACCAG | GATGCCATTG | CTGTGGAAGC | TGCCTGCACT | AATGTTCCGG |
| 3551 | CGTTATTTCT | TGATGTCTCT | GACCAGACAC | CCATCAACAG | TATTATTTTC |
| 3601 | TCCCATGAAG | ACGGTACGCG | ACTGGGCGTG | GAGCATCTGG | TCGCATTGGG |
| 3651 | TCACCAGCAA | ATCGCGCTGT | TAGCGGGCCC | ATTAAGTTCT | GTCTCGGCGC |
| 3701 | GTCTGCGTCT | GGCTGGCTGG | CATAAATATC | TCACTCGCAA | TCAAATTCAG |
| 3751 | CCGATAGCGG | AACGGGAAGG | CGACTGGAGT | GCCATGTCCG | GTTTTCAACA |
| 3801 | AACCATGCAA | ATGCTGAATG | AGGGCATCGT | TCCCACTGCG | ATGCTGGTTG |

TAB. 5-continued

| | | Sequence 7/1 | | |
|---|---|---|---|---|
| 3851 | CCAACGATCA | GATGGCGCTG | GGCGCAATGC | GCGCCATTAC | CGAGTCCGGG |
| 3901 | CTGCGCGTTG | GTGCGGATAT | CTCGGTAGTG | GGATACGACG | ATACCGAAGA |
| 3951 | CAGCTCATGT | TATATCCCGC | CGTCAACCAC | CATCAAACAG | GATTTTCGCC |
| 4001 | TGCTGGGGCA | AACCAGCGTG | GACCGCTTGC | TGCAACTCTC | TCAGGGCCAG |
| 4051 | GCGGTGAAGG | GCAATCAGCT | GTTGCCCGTC | TCACTGGTGA | AAAGAAAAAC |
| 4101 | CACCCTGGCG | CCCAATACGC | AAACCGCCTC | TCCCCGCGCG | TTGGCCGATT |
| 4151 | CATTAATGCA | GCTGGCACGA | CAGGTTTCCC | GACTGGAAAG | CGGGCAGTGA |
| 4201 | GCGCAACGCA | ATTAATGTGA | GTTAGCGCGA | ATTGATCTG | |

We claim:

1. A fusion peptide consisting of a signal peptide from *Bordetella pertussis* fused to a heterologous protein, wherein said signal peptide has the following amino acid sequence:

M K K W F V A A G I G A G L L M L S S A A.

* * * * *